United States Patent [19]
Davidson

[11] Patent Number: 6,159,474
[45] Date of Patent: Dec. 12, 2000

[54] ANIMAL REPELLANT CONTAINING OILS OF BLACK PEPPER AND/OR CAPSICUM

[76] Inventor: Ted Davidson, 154 Grand-Rang, St. Basile, Quebec, Canada, G0A-3G0

[21] Appl. No.: 09/124,724

[22] Filed: Jul. 29, 1998

Related U.S. Application Data

[63] Continuation-in-part of application No. 08/639,771, Apr. 29, 1996, abandoned.

[30] Foreign Application Priority Data

May 1, 1995 [CA] Canada .................................. 2148338

[51] Int. Cl.$^7$ .................................... A01N 65/00
[52] U.S. Cl. ........................ 424/195.1; 514/919; 514/920; 514/552
[58] Field of Search ........................ 424/195.1; 514/919, 514/920, 552

[56] References Cited

U.S. PATENT DOCUMENTS

| | | | |
|---|---|---|---|
| 631,738 | 8/1899 | Dowie | 424/195.1 |
| 5,500,205 | 3/1996 | Abbott | 424/195.1 |
| 5,698,191 | 12/1997 | Wiersma | 424/195.1 |

FOREIGN PATENT DOCUMENTS 2546718   12/1984   France .

OTHER PUBLICATIONS

Mansour et al., Phytoparasitica (1986), 14(2), 137–42.
Houpt et al., Am J Vet Res 45 (8). 1984. 1501–1503.

*Primary Examiner*—Irene Marx
*Attorney, Agent, or Firm*—Eric Fincham

[57] ABSTRACT

A repellant composition for repelling both domesticated and wild animals which comprises between 0.05% and 2% by weight of an essential oil of either black pepper or capsicum and between 0.1% and 10% by weight of an oleoresin of either black pepper or capsicum and an antioxidant in an amount sufficient to stabilize the oleoresin. Preferably, the carrier is a finely divided inert solid material and the composition includes a binder such as lard. The composition can be spread on the ground and maintains its effectiveness over an extended period of time.

14 Claims, No Drawings

ANIMAL REPELLANT CONTAINING OILS OF BLACK PEPPER AND/OR CAPSICUM

The present application is a continuation-in-part of application Ser. No. 08/639,771 filed Apr. 29, 1996 now abandoned.

BACKGROUND OF THE INVENTION

The present invention relates to repellant compositions, a method of repelling animals and a method of manufacture of a repellant composition.

Various types of repellant compositions are well known in the art. The nature of the repellant composition will vary depending upon the species of animal, bird or insect which it is intended to repel. Many of the known repellants are based on man made chemicals and for this reason, are not considered desirable for ecological reasons. Various repellant compositions have also been proposed which are environmentally friendly in that they utilize naturally occurring ingredients. Among such repellants are those shown in U.S. Pat. No. 4,455,304 which teaches the use of a composition for repelling birds, the patentee teaching a composition which includes a finely divided garlic constituent and a finely divided cayenne pepper constituent. The patentee notes that neither black pepper nor white pepper are suitable for use.

U.S. Pat. No. 4,795,637 teaches the use of a rodent repellant powder which uses a thujone oil with a powder which can be selected from a number of different products including tobacco dust, pepper powder, sulphur powder, etc. The thujone oil is derived from the cedar tree and is the natural repellant.

It is also known from U.S. Pat. No. 4,820,517 to use a pepper extract as an insecticide. The toxicity of black pepper has been previously known, from, U.S. Pat. No. 779,634 to Allen.

It is also known from WO 95/07024 to provide insect repellants using pyrethrin as an active ingredient.

While some of the above compositions are suggested as being suitable repellants for insects, there are no teachings of the use of a repellant which can cover a number of different larger species of animals such as dogs, cats, raccoons, skunks, mice, rats, squirrels, chipmunks, deer, etc. and which utilizes naturally occurring compounds for ecological reasons.

SUMMARY OF THE INVENTION

It is an object of the present invention to provide a repellant which utilizes naturally occurring ingredients.

It is a further object of the present invention to provide a repellant using naturally occurring ingredients and which repellant is effective against animals and which repellant has minimal toxicity.

It is a further object of the present invention to provide a method for naturally repelling both domestic and other animals having an olfactory capability.

It is a further object of the present invention to provide a method of manufacture of a repellant having naturally occurring ingredients.

It is a further object of the present invention to provide a repellant which is both long lasting and environmentally friendly.

According to one aspect of the present invention, there is provided a repellant composition comprising a carrier; between 0.05% and 2% by weight of an essential oil selected from the group consisting of the essential oils of black pepper and capsicum; between 0.1% and 10% by weight of an oleoresin selected from the group consisting of the oleoresins of black pepper and capsicum; and an antioxidant in an amount sufficient to stabilize the oleoresin and essential oil.

In a further aspect of the present invention, there is provided a repellant composition as set forth above wherein the carrier is of a finely divided inert solid material and further comprising lard in an amount of between 0.5% and 4% by weight, the lard acting to bind the essential oil, the oleoresin and the antioxidant to the carrier, and further including a moisture retaining agent comprised of mixed dried ground evergreen needles, the essential oil being the essential oil of black pepper present in an amount of between 0.1% and 0.75% by weight, the oleoresin being the oleoresin of capsicum present in an amount of between 0.25% and 2.25% by weight, the oleoresin of capsicum having a minimum of 40,000 scoville heat units, the antioxidant being an oleoresin of rosemary present in an amount of between 0.04% and 0.07% by weight.

In a still further aspect of the present invention, there is provided a method for repelling animals, the method comprising the steps of applying to an area to be protected an effective amount to repel a desired animal a composition comprised of a carrier of a finely divided inert solid material; between 0.05% and 2.0% by weight of an essential oil selected from the group consisting of the essential oils of black pepper and capsicum; between 0.1% and 10% by weight of an oleoresin selected from the group consisting of the oleoresins of black pepper and capsicum; an antioxidant in an amount sufficient to stabilize the oleoresin and essential oil without neutralizing the repellant properties of the oleoresin and essential oil; a binder to retain the essential oil, the oleoresin and the antioxidant on the carrier; and a moisture retaining agent having liquid absorbing and liquid retention properties.

In a still further aspect of the present invention, there is provided a method of manufacture of a repellant which comprises the steps of mixing between 0.05% and 2% by weight of an essential oil selected from the group consisting of the essential oils of black pepper and capsicum, between 0.1% and 10% by weight of an oleoresin selected from the group consisting of the oleoresins of black pepper and capsicum, an antioxidant in an amount sufficient to stabilize the oleoresin and essential oil without neutralizing the oleoresin and essential oil, and a binder to bind the essential oil, the oleoresin and the antioxidant, and subsequently adding a carrier of a finely divided inert solid material.

DESCRIPTION OF THE PREFERRED EMBODIMENTS

In greater detail, the repellant of the present invention is adapted to be used for a wide variety of animal species. As such, for the animal species, it can be utilized for both domestic and wild animals which have an olfactory capability, including such animals as dogs, cats, deer, skunks, raccoons, groundhogs, gophers, etc. Use of the repellant has also been found to be effective against some species of birds, including, for example, pigeons, geese, etc.

The composition utilizes, in combination, two different active ingredients; an oleoresin selected from the group consisting of black pepper and capsicum, and an essential oil of either black pepper or capsicum. Black pepper is classified as the genus Piper, species Piper Nigrum, and is the product of a shrub grown in a hot climate. The plant bears a small berry which is picked before it ripens and then dried.

The present invention may use two components of the black pepper, both of which components are commercially available. Thus, the present invention may utilize, as two of the chemically active ingredients, an oleoresin selected from the group consisting of black pepper and capsicum, and also an essential oil of either black pepper or capsicum.

The amount of the oleoresin and the essential oil may be varied and it is well within the skill of one knowledgeable in the art to so do. In preferred embodiments of the invention, the oleoresin will be present in an amount of between 0.1 to 10% by weight of the composition and preferably between 0.25% and 2.25% in even more preferred embodiments, would be present in a range of between 1.0% and 1.5% by weight. The oleoresin preferably has at least 5,000 scoville heat units and more preferably in excess of 40,000 scoville heat units. The essential oil is preferably present in a weight percentage of between 0.05 and 2% or preferably between 0.1% and 0.75% and even more preferably, between 0.2% and 0.3% by weight.

In one embodiment, the oleoresin and essential oil or oils are dissolved in an oil component (binder) and then utilized with a suitable carrier. The particular oil can be selected from among many known suitable oils and in a preferred embodiment, the oil is a vegetable type oil. Among suitable vegetable oils are canola oil, soy oil, corn oil, etc. Naturally, the cost associated with the particular oil would be a primary consideration. The oil, in the preferred embodiments, would be present in a weight percentage of between 0.5% and 4%. In a particularly preferred embodiment, lard is used as a binder between the carrier and other components. The components can be incorporated with the lard when it is in a liquid state while at normal ambient temperatures, it is in a semi-solid state and thus acts to retain the components on the carrier even under rainy conditions. As will be understood from the above, the binder must be capable of "dissolving" the active ingredients and also be of a relatively viscous nature.

The composition can be utilized with any suitable carrier and the particular carrier will naturally depend upon the method of application. While the composition could be applied as sprays and the like, the life span would be limited. It is preferred that it be applied with a solid carrier such that the composition will remain and not soak into the ground or be washed away. Naturally, for ecological reasons, it is highly preferable that the carrier be a naturally occurring one and one which can adsorb the oil mixture. For broadcasting over a wide area, a preferred carrier is a finally divided sifted dry sand or stone dust or powder. This carrier has the capability of adsorbing the oil mixture and being a naturally occurring product, is environmentally friendly. The carrier preferably has a grit size of between 12 and 20 grit and preferably is 16 grit. The carrier material may form, as a weight percentage of the total composition, between 50% and 98%. In the case of a liquid formulation, water soluble concentrates and, if required, a suitable emulsifier/solvent could be employed.

Naturally, many other known materials can be added to the repellant. Thus, various extenders and/or products having different activities may be associated therewith. One such possibility would be the use of fertilizers and/or conditioners when the repellant is applied to relatively large areas such as lawns or the like.

Preferred embodiments of the invention include the use of other components in the composition. Thus, in one preferred embodiment, one may add the oleoresin of rosemary. Rosemary is an evergreen shrub of the mint family Labiatae and is classified as genus Rosmarinus species Rosmarinus Officinalis. The plant is widely used as a herb and is also used in perfumes. The use of the oleoresin of rosemary is desirable for providing a longer lasting effect to the repellant composition.

In this respect, the oleoresin of rosemary functions as an antioxidant to stabilize the oleoresin and essential oil. For example, the oleoresin of capsicum will normally oxidize within 48 hours if it is not stabilized. The oleoresin of rosemary can also act to stabilize lard when it is used as the binder.

The percentage of the oleoresin of rosemary is critical. It must be used in an amount sufficient to perform its function as an antioxidant while too large an amount of rosemary will tend to neutralize the active repellant components. In general, the oleoresin of rosemary would be present in an amount of between 0.01% and 0.25% by weight and most preferably is present in an amount of between 0.04% and 0.07% by weight.

The repellant composition is most effective in a humid and damp environment. After three or four days in a dry environment, the action of the essential oil appears to be less effective. Upon the addition of moisture, the aroma from the essential oil is reactivated. To this end, the composition will preferably include a moisture retention agent which has the properties of being capable of absorbing a liquid and retaining a liquid. While different products such as peat moss are capable of doing the same, a preferred moisture retention agent is the ends of evergreen branches. These evergreen branch ends are introduced into a vapor still and the essential oils extracted. The remaining organic wastes are dried and mulched into a powder form. Such a product is marketed under the trademark "MOUKA" and which MOUKA™ comprises approximately 65% of a cedar component and 35% of a mixed spruce/fir component. The cedar component provides a certain insecticidal activity upon decomposition of the same. The water retention agent is preferably present in an amount of between 2% and 20% by weight.

Without being limited to any particular theory, the composition of the present invention appears to act on the sinuses of the animal. In particular, it is believed that the essential oils provide an olfactory deterrent. Should the animal then attempt to taste the material, the oleoresin will reinforce the linkage between the smell and the undesirability of the same.

The manufacture of the product can be easily accomplished using conventional equipment. First, the oils and oleoresin are mixed together with the chemically active ingredients being oil soluble. Subsequently, the oil and carrier may be mixed and the MOUKA™ (if used) added.

The following examples will provide illustrations of the use of the invention.

EXAMPLE 1

A composition was prepared according to the following formula

|  | Quantity (Weight %) |
|---|---|
| Oleoresin of black pepper | 1.25 |
| Essential oil of black pepper | 0.25 |
| Oleoresin of rosemary | 0.06 |
| Vegetable oil (canola) | 1.44 |
| MOUKA TM | 10.00 |
| Powdered stone (up to ⅛" diam.) | 87.00 |

The black pepper oleoresin, the essential oil of black pepper, the oleoresin of rosemary and the vegetable oil were mixed. Subsequently, the powdered stone was introduced and subsequently the MOUKA™ was added and mixed. The composition was applied at a rate of 1 kilogram per 60 square feet to a four foot width of a grassy area beside a sidewalk at a university. This was site was selected as it was very popular with residents as a place to take their pets and particularly dogs.

The local caretakers reported a significant decrease in the amount of animal excrement found on the site to which the composition was applied. The composition was applied during the month of June and was found to be effective for a period of approximately 135 days.

EXAMPLE 2

A composition was prepared according to the following formula

|  | Quantity (Weight %) |
|---|---|
| Oleoresin of capsicum | 0.75 |
| Essential oil of capsicum | 0.75 |
| Oleoresin of rosemary | 0.06 |
| Lard | 1.44 |
| MOUKA TM | 10.00 |
| Sifted dry sand (16 grit) | 87.00 |

The essential oil of capsicum, the oleoresin of capsicum and the oleoresin of rosemary were mixed with the lard at a temperature of approximately 850° C. The mixture was then sprayed on the sifted dry sand and allowed to cool. Subsequently, the MOUKA™ was added and mixed.

The composition was then applied at an approximate rate of 1 kilogram per 6 square meters at a park area where problems with domestic animals and particularly dogs was reported. There was a significant decrease in the use of the area by the domestic animals and this continued for a period of time in excess of 60 days.

It will be understood that the above described embodiments are for purposes of illustration only and that changes and modifications may be made thereto without departing from the spirit and scope of the invention.

I claim:

1. A repellant composition for animals comprising:
   between 50% and 98% by weight of a carrier of a finely divided inert solid material;
   between 0.05% and 2% by weigh of an essential oil selected from the group consisting of the essential oils of black pepper and capsicum;
   between 0.1% and 10% by weight of an oleoresin selected from the group consisting of the oleoresins of black pepper and capsicum;
   between 0.01% and 0.25% of an antioxidant in an amount sufficient to stabilize said oleoresin and said essential oil;
   between 0.5% and 4% of a binder to bind said essential oil, said oleoresin and said antioxidant to said carrier; and
   between 2% and 2.0% of a moisture retaining agent, said moisture retaining agent having liquid absorbing and liquid retention properties.

2. The composition of claim 1 wherein said essential oil is present in an amount of between 0.1% and 0.75% by weight and said oleoresin is present in an amount of between 0.25% and 2.25% by weight.

3. The composition of claim 2 wherein said antioxidant comprises an oleoresin of rosemary, said oleoresin of rosemary being present in an amount of between 0.01% and 0.25% by weight.

4. The composition of claim 2 wherein said oleoresin of rosemary is present in an amount of between 0.04% and 0.07% by weight.

5. The composition of claim 2 wherein said moisture retaining agent comprises dried ground evergreen needles.

6. The composition of claim 1 wherein said binder comprises lard.

7. The composition of claim 1 wherein said carrier comprises a sifted dry sand having a size of between 12 grit and 20 grit.

8. The composition of claim 2 wherein said essential oil comprises the essential oil of black pepper, said essential oil being present in an amount of between 0.1% and 0.75% by weight.

9. The composition of claim 1 wherein said oleoresin comprises the oleoresin of capsicum, said oleoresin being present in an amount of between 0.25% and 2.25% by weight.

10. The composition of claim 9 wherein said oleoresin of capsicum has a minimum of 5,000 scoville heat units.

11. The composition of claim 9 wherein said oleoresin of capsicum has a minimum of 40,000 scoville heat units.

12. The repellant composition of claim 1 wherein said binder is lard, said moisture retaining agent comprises mixed dried ground evergreen needles, said essential oil being the essential oil of black pepper present in an amount of between 0.1% and 0.75% by weight, said oleoresin being the oleoresin of capsicum present in an amount of between 0.25% and 2.25% by weight, said oleoresin of capsicum having a minimum of 40,000 scoville heat units, said antioxidant being an oleoresin of rosemary present in an amount of between 0.04% and 0.07% by weight.

13. A method for repelling animals, the method comprising the steps of applying to an area to be protected an effective amount to repel a desired animal of a composition comprised of between 50% and 98% by weight of a carrier of a finely divided inert solid material; between 0.05% and 2.0% by weight of an essential oil selected from the group consisting of the essential oils of black pepper and capsicum; between 0.1% and 10% by weight of an oleoresin selected from the group consisting of the oleoresins of black pepper and capsicum; between 0.04% and 0.07% by weight of an oleoresin of rosemary; between 0.5% and 4% by weight of a binder to retain said essential oil and said oleoresins on said carrier; and between 2% and 20% by weight of a moisture retaining agent having liquid absorbing and liquid retention properties.

14. A method of manufacture of a repellant which comprises the steps of mixing between 0.05% and 2% by weight of a essential oil selected from the group consisting of the essential oils of black pepper and capsicum, between 0.1% and 10% by weight of an oleoresin selected from the group consisting of the oleoresins of black pepper and capsicum, between 0.04% and 0.07% By weight of an oleoresin of rosemary, and between 0.5% and 4% by weight of a binder to bind said essential oil and said oleoresins, and subsequently adding between 50% and 98% by weight of a carrier of a finely divided inert solid material.

* * * * *

UNITED STATES PATENT AND TRADEMARK OFFICE
CERTIFICATE OF CORRECTION

PATENT NO.    : 6,159,474
DATED         : December 12, 2000
INVENTOR(S)   : Ted Davidson It is certified that error appears in the above-identified patent and that said Letters Patent is hereby corrected as shown below:

<u>Column 5,</u>
Line 41, change "weigh" to -- weight --.
Line 53, change "2.0%" to -- 20% --

Signed and Sealed this

Twenty-sixth Day of March, 2002

Attest:

Attesting Officer

JAMES E. ROGAN
*Director of the United States Patent and Trademark Office*